United States Patent [19]
Jost

[11] Patent Number: 4,592,748
[45] Date of Patent: Jun. 3, 1986

[54] YOGHURT BASED DOUCHE KIT AND ASSEMBLY THEREFOR

[75] Inventor: Leonora Jost, New York, N.Y.

[73] Assignee: Vortex Research Corp., New York, N.Y.

[21] Appl. No.: 612,065

[22] Filed: May 18, 1984

[51] Int. Cl.⁴ ............................................ A61M 31/00
[52] U.S. Cl. .................................................... 604/279
[58] Field of Search ........................... 167/58; 604/279

[56] References Cited
U.S. PATENT DOCUMENTS 3,346,451 10/1967 Collins et al. ......................... 167/58

OTHER PUBLICATIONS

CA77(19) 125047, Blanchaud, 1972, "Concentrated or Dried Yoghurt".

Primary Examiner—Ferris H. Lander
Attorney, Agent, or Firm—Sheldon Palmer

[57] ABSTRACT

A dry, active, acidic yoghurt based douching product is prepared by lyophilizing yoghurt made from bovine milk and pure cultures of *Lactobacillus acidophilus, Lactobacillus helveticus* and *Streptococcus lactis*. Also disclosed is a disposable douche kit including packets containing pre-measured doses of the yoghurt based product and a container (10) and nozzle (20) assembly so configured as to enable the kit to be used under the flow of gravity rather than under pressure and at the same time prevent douching material from entering the uterus.

6 Claims, 2 Drawing Figures

YOGHURT BASED DOUCHE KIT AND ASSEMBLY THEREFOR

BACKGROUND OF THE INVENTION

1. Field of the Invention

The present invention relates to disposable douches and, more particularly, to a disposable douche based on a yoghurt product.

2. The Prior Art

Disposable douches are of course well known. These, however, suffer from one or more drawbacks resulting from the fact that all of them are contained in pressure type containers which, in use, are squeezed to force the contents into the vaginal cavity. This technique invariably causes air to also be forced into the vaginal cavity and thence into the uterus where there is a significant danger of an air embolism getting into the bloodstream and causing injury or death.

The present douche, in addition to being based on a natural product having no adverse effects and an optimum PH regulating capacity also avoids the potential danger from air emboli which characterize the prior douches.

SUMMARY OF THE INVENTION

Figure 1:
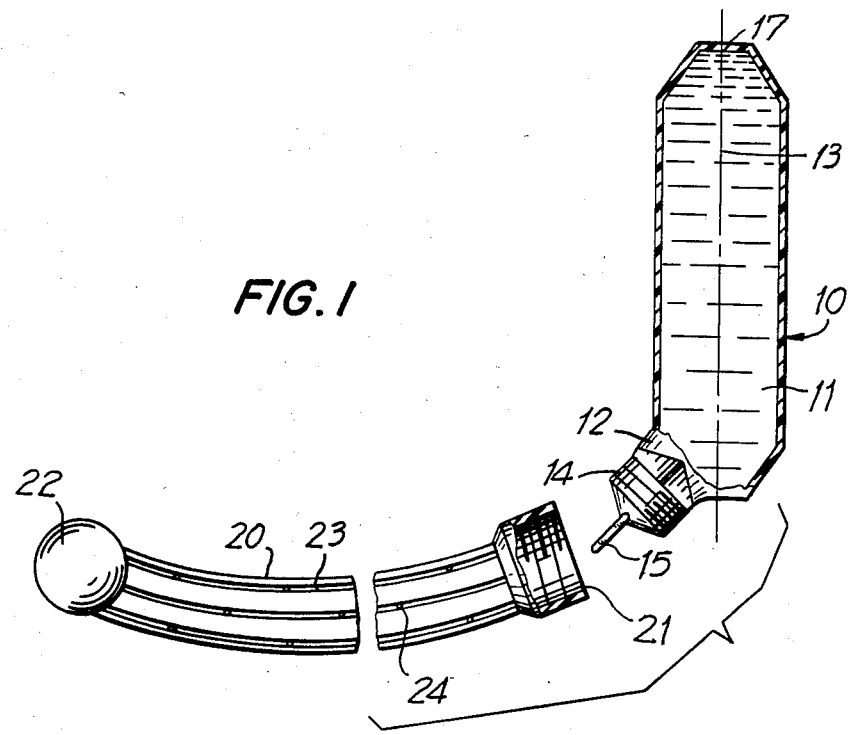
FIG. 1 is a side view of a container and nozzle assembly (shown disassembled) portion of a douche kit according to the invention.
Figure 2:
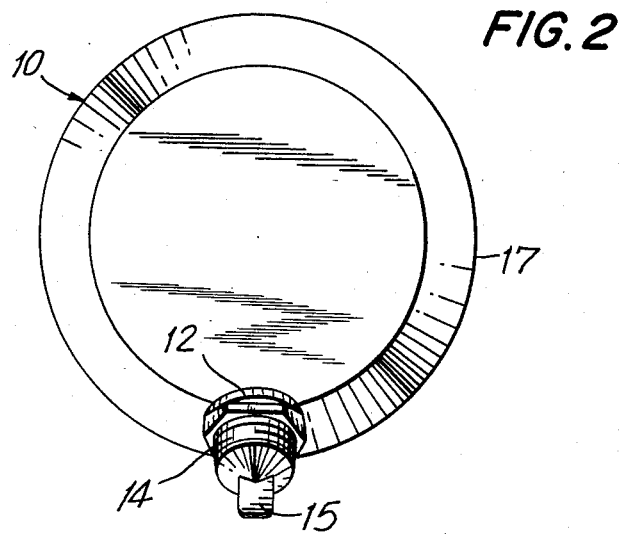
FIG. 2 is an enlarged, front end view of the container.

The invention provides, in one aspect thereof, a dry, active, acidic yoghurt based product for douching made by lyophilizing yoghurt made from bovine milk and pure cultures of *Lactobacillus acidophilus, Lactobacillus helveticus* and *Streptococcus lactis*.

The invention also provides a disposable douche kit including pre-measured doses of the yoghurt based product, a sealed container having purified water therein and a specially designed nozzle adapted to fit on the container after the seal is broken and the pre-measured dose of the yoghurt based product is added thereto. Because of the configuration of the container and nozzle assembly, the kit, when used results in the douching material being introduced into the vaginal cavity under the flow of gravity rather than under pressure.

DETAILED DESCRIPTION OF THE INVENTION

There will be described, in order, the preparation of the yoghurt produced used as the active douching material, the construction of the container and nozzle assembly for using the yoghurt product in douching and the use of the douche kit.

The Yoghurt Product

The starting material for making the yoghurt product is uncultured whole or skim bovine milk. To such milk there are added individual portions of pure cultures of three different strains of lactic acid bacteria. These are *Lactobacillus acidophilus, Lactobacillus helveticus* and *Streptococcus lactis*. The amount of each strain added is 0.1 g per liter of milk. The milk containing the added bacteria is then incubated at a temperature of about 78°–80° F. for a period of time sufficient to allow the milk to coagulate. This is generally about 12–18 hours. If skim milk is used, or if whole milk containing reconstituted milk is used, this may take a longer period, i.e., up to about 24 hours. At the end of the incubation period, the resulting product which is yoghurt is then subjected to a conventional lyophilization (freeze drying) process to form a dry powder. This powder is put through a very fine micromesh screen to form an ultrafine powder which is almost instantaneously completely dispersible in water without clumping. This characteristic is important in connection with the eventual use of the product.

When subjected to various analyses, the dry powder product has the following characteristics:

| A. | Physico-Chemical Characteristics | |
|---|---|---|
| | appearance | soft powder |
| | color | yellow white |
| | smell | milk powder |
| | pH | 3.7–4.2 |
| | solubility | 88.0% |
| B. | Chemical Characteristics (% by weight) | |
| | protein | >13.0 |
| | fat | 1–1.5 |
| | ash | >9.5 |
| | cellulosic matter | <0.5 |
| | non nitrogen matter | 66–68 |
| | Calcium | 1.10–1.30 |
| | Phosphorus | 0.75–0.85 |
| C. | Amino-Acids (g per 100 g of product) | |
| | Methionine | 0.41 |
| | Methionine + cystine | 0.67 |
| | Lysine | 1.53 |
| | Threonine | 1.02 |
| | Tryptophan | 0.28 |
| D. | Lactic Acid Bacteria | |
| | (1) Strains: | *Lactobacillus Acidophilus* *Lactobacillus Helveticus* *Streptococcus Lactis* |
| | (2) Activity: | $2 \times 10^8$ active germs per gram of product |
| | (3) Microbiological Lysate: | $10^9$ germs per gram of product (inactive, i.e. non lactobacillus |
| E. | Bacteriological Characteristics | |
| | Coliform bacteria | <5% |
| | sulfite reductant clostridium | <5% |
| | *Clostridium perfringens* | 0 |

The above described dry yoghurt product is then vacuum packed using conventional techniques in individual plastic lined aluminum foil packets each containing 0.5–0.7 g. This amount of product is intended to be used as a single "dose" for douching purposes with about 4.5–5.0 ounces of water as described below.

The Container and Nozzle Assembly

As shown in FIG. 1, the container and nozzle assembly comprises a container 10 and a nozzle 20. Container 10, which is molded from low density polyethylene or polypropylene (as is the nozzle), includes a generally elongate body portion 11 and a neck portion 12 which is set at an angle of about 135° to the longitudinal axis 13 of body portion 11. The significance of this configuration will be described below. Neck portion 12 includes threaded portion 14 adapted to be threaded into complementary threads on the nozzle. The outer perimeter of neck portion 12 is preferably hexagonal in cross-section so as to prevent it from being squeezed during use. This is important because it is intended for the douching material to enter the vaginal cavity by gravity rather than under pressure. Threaded portion 14 terminates in an integrally formed seal 15 which is secured to the container 10 after it is formed by molding and filled with purified water 16. Container 10 is about 3½ inches in length and about 1¾ inches in diameter. These dimensions provide for a volume of about 4½–5 fluid ounces. When ready for use, container 10 is opened by breaking seal 15.

Nozzle 20 is a hollow curved, elongate tube about 7 inches in length, the rate of curvature being anatomically compatible with insertion of the nozzle 20 into a vagina for substantially the entire length of the nozzle. The open end 21 of nozzle 20 is provided with threads complementing those on container 10. The distal end of nozzle 20 is formed into a closed spherical element 22 of about ¾ to ⅞ inches so that when nozzle 20 is fully inserted into the user's vagina, spherical element 21 abuts the cervical os and isolates it temporarily from the vaginal chamber. Because of this configuration, the douching material will only flood the vaginal cavity and will be prevented from entering the uterus through the os. Nozzle 20 is provided with a plurality of, preferably six, longitudinal channels 23 equally spaced about the circumference of the nozzle 20 and each having four holes 24 of about ⅛ inch diameter which preferably are staggered relative to the holes provided in the adjacent channel.

The Use of the Douche Kit

To properly use the douche kit of the invention, the user will open container 10 by breaking seal 15 and add to the container 10 the contents of one of the packages (containing ca. 0.5 g of the dry powder). The opening of the container is sealed by placing a finger tip over the opening and shaking the contents to form a slurry. Nozzle 20 is then screwed onto container 10 and the container is then laid on its flat side with the nozzle 20 pointing up. The assembled container and nozzle should then be left standing at room temperature for about 5–10 minutes to enable the slurry to become viscous.

The user, while standing up or squatting on a toilet, should then hold the assembled kit in an upright position, in front of her mons veneris, i.e., with the closed end 17 of the container 10 pointing upward and the spherical element 22 pointing in the direction of vaginal opening. Before inserting nozzle 20 into the vagina, the flow of douching material should be started by gentle manual pressure on the container 10. The purpose of this is to force any air which is present in the neck portion 12 and nozzle 20 out of the kit. Since the douching material is very viscous, the flow will be rather slow and continuous. At this point, the nozzle should be inserted all the way into the vaginal cavity and the flow of the douching material permitted to continue under the action of gravity rather than by pressure.

The use of the douching kit of the present invention as opposed to more conventional disposable douches has several advantages. For one thing, the use of the current methods and devices is largely cosmetic and aesthetic in nature. While there is nothing objectionable per se connected with douching for cosmetic purposes, this fails to address the problems, both real and potential. Under normal conditions, the vagina is slightly acidic. It is important for health reasons to maintain a proper pH balance in the vagina. That balance is often disturbed when a woman has had, for example, a yeast infection (which is very common) or cystitis. It is also disturbed by the ingestion of large doses of antibiotics which may have been taken for non-related illnesses. The use of the acidic yoghurt based preparation of the present invention overcomes this problem.

In addition, and as stated above, most, if not all, presently available douche kits are of the pressure type. This may lead to the formation of potentially fatal air emboli. In contrast, the present douche kit is gravity fed and this substantially completely eliminates air in the system when properly used.

Variations and modifications can, of course, be made without departing from the spirit and scope of the present invention.

Having thus described my invention what I desire to secure by Letters Patent and hereby claim is:

1. A lyophilized yoghurt product for use, in an aqueous dispersion, as a vaginal or anal douche, said yoghurt product being produced by a method which comprises adding to bovine milk pure, cultured *Lactobacillus acidophilus, Lactobacillus helveticus* and *Streptococcus lactis,* each in an amount of 0.1 g per liter of milk, culturing the resulting mixture at about 78°–80° F. for a period of time sufficient to cause coagulation and thereby form a yoghurt and lyophilizing the resulting yoghurt to form a dry powdered product.

2. A yoghurt product according to claim 1 wherein culturing is effected for about 12–18 hours and the dry powdered product is seived through a micro size mesh.

3. A one-time use package comprising about 0.5–0.67 g of the product according to claim 1 in a vacuum packed plastic lined aluminum foil packet.

4. A package according to claim 3 wherein the plastic liner is polypropylene or polyethylene.

5. A one-time use, disposable douche kit comprising a package according to claim 3 and a container and nozzle assembly, said container being a low density polyethylene or polypropylene sealed bottle containing about 4½ to 5 ounces of purified water, said bottle being adapted, after having had its seal broken, to receive a threaded, elongate, curved nozzle, said nozzle having a plurality of holes spaced along the length thereof and, at its distal end, a spherical configuration so dimensioned and so placed as to cover the cervical os when the nozzle is inserted vaginally, thereby restricting the douche to the vaginal cavity and preventing the douche from entering the uterus.

6. A kit according to claim 5 wherein the bottle comprises an elongate body portion and a neck portion set at an angle of about 135° to the longitudinal axis of the body portion so that when the elongate, curved nozzle is attached to the neck, the configuration of the assembled bottle and nozzle is such that when the kit is in use by a woman in a standing or squatting position, the elongate body portion of the bottle is generally parallel to the surface of her torso.

* * * * *